United States Patent
Barofsky

(10) Patent No.: US 11,020,279 B2
(45) Date of Patent: Jun. 1, 2021

(54) WOUND STASIS DRESSING FOR LARGE SURFACE WOUNDS

(71) Applicant: RevMedx, Inc., Wilsonville, OR (US)

(72) Inventor: Andrew Barofsky, Lake Oswego, OR (US)

(73) Assignee: RevMedx, Inc., Wilsonville, OR (US)

( * ) Notice: Subject to any disclaimer, the term of this patent is extended or adjusted under 35 U.S.C. 154(b) by 0 days.

(21) Appl. No.: 15/796,663

(22) Filed: Oct. 27, 2017

(65) Prior Publication Data

US 2018/0071149 A1 Mar. 15, 2018

Related U.S. Application Data

(63) Continuation of application No. 13/398,671, filed on Feb. 16, 2012, now abandoned.

(60) Provisional application No. 61/525,036, filed on Aug. 18, 2011, provisional application No. 61/443,520, filed on Feb. 16, 2011.

(51) Int. Cl.
*A61F 13/02* (2006.01)
*A61F 13/00* (2006.01)

(52) U.S. Cl.
CPC .... *A61F 13/0243* (2013.01); *A61F 13/00051* (2013.01); *A61F 13/0233* (2013.01); *A61F 2013/00463* (2013.01); *A61F 2013/00468* (2013.01)

(58) Field of Classification Search
CPC .... A61F 2013/530649; A61F 13/00042; A61F 13/0206; A61F 13/0223; A61F 2013/00463; A61F 2013/00468; A61F 13/0233; A61F 13/0243
See application file for complete search history.

(56) References Cited

U.S. PATENT DOCUMENTS

| | | |
|---|---|---|
| 3,835,992 A | 9/1974 | Adams |
| 5,383,891 A | 1/1995 | Walker |
| 6,027,471 A | 2/2000 | Fallon et al. |
| 6,964,658 B2 | 11/2005 | Ashby et al. |
| 7,709,631 B2 | 5/2010 | Harris |

(Continued)

FOREIGN PATENT DOCUMENTS

| | | |
|---|---|---|
| EP | 2319471 | 5/2011 |
| WO | 2000/029484 | 5/2000 |

(Continued)

OTHER PUBLICATIONS

Kraus, David. "Proposal to Reclassify the Absorbable Homeostatic Agent Device, Memo to General and Plastic Surgery Devices Panel Members," Food and Drug Administration, Jun. 4, 2002; pp. 1-8.

(Continued)

*Primary Examiner* — Kortney L. Klinkel
(74) *Attorney, Agent, or Firm* — Schwabe, Williamson & Wyatt, P.C.

(57) ABSTRACT

Embodiments herein provide hemostatic compositions comprising a plurality of liquid-expandable articles arranged on a backing material. In general, embodiments include methods for treating hemorrhagic injuries. More specifically, there is provided a method to effect rapid hemostatic response and control hemorrhage by introducing a hemostatic composition into a bleeding wound cavity. An embodiment also provides a method of preparing or manufacturing such a hemostatic composition.

14 Claims, 5 Drawing Sheets

(56) References Cited

U.S. PATENT DOCUMENTS

| | | |
|---|---|---|
| 8,828,050 B2 | 9/2014 | Gregory et al. |
| 2003/0095997 A1 | 5/2003 | Ruszczak et al. |
| 2003/0202970 A1 | 10/2003 | Liu et al. |
| 2004/0013715 A1 | 1/2004 | Wnek et al. |
| 2004/0122350 A1 | 6/2004 | Zhong et al. |
| 2006/0004408 A1 | 1/2006 | Morris et al. |
| 2006/0173492 A1 | 8/2006 | Akerfeldt et al. |
| 2006/0233869 A1 | 10/2006 | Looney et al. |
| 2007/0014862 A1 | 1/2007 | Pameijer et al. |
| 2007/0021703 A1 | 1/2007 | McCarthy |
| 2007/0100271 A1 | 5/2007 | Shimanuki |
| 2007/0148161 A1 | 6/2007 | Delmotte |
| 2007/0255238 A1 | 11/2007 | Cochrum et al. |
| 2008/0071207 A1 | 3/2008 | deLuis et al. |
| 2008/0171958 A1 | 7/2008 | Gundersen |
| 2009/0226391 A1 | 9/2009 | Roberts et al. |
| 2009/0270827 A1* | 10/2009 | Gundersen .......... A61F 13/0276 604/369 |
| 2010/0129247 A1 | 5/2010 | Hen et al. |
| 2014/0142523 A1 | 5/2014 | Steinbaugh |

FOREIGN PATENT DOCUMENTS

| | | |
|---|---|---|
| WO | 2002/022059 | 3/2002 |
| WO | 2010-129587 | 11/2010 |
| WO | 2012-112797 | 2/2013 |

OTHER PUBLICATIONS

Batuno, T., et al., "New Collagen Topical Homeostatic Agent-Comparative Evaluation in Experimental Animal Wounds," Jpn J Artif Organs. 1990, vol. 19, No. 3, pp. 1235-1238.

* cited by examiner

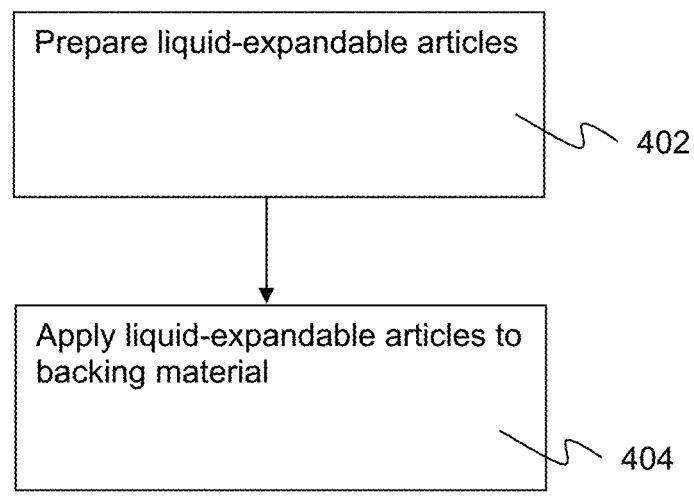
FIG. 4
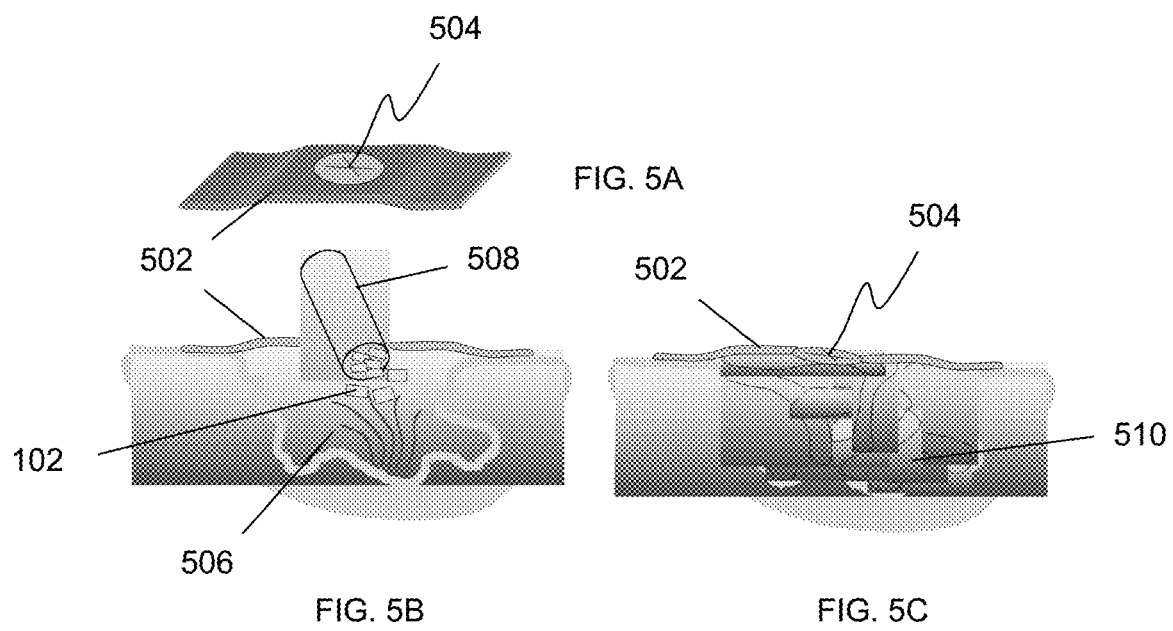
FIG. 5A
FIG. 5B
FIG. 5C

WOUND STASIS DRESSING FOR LARGE SURFACE WOUNDS

CROSS REFERENCE TO RELATED APPLICATIONS

The present application is a divisional of and claims priority to U.S. patent application Ser. No. 13/398,671, filed Feb. 16, 2012 entitled "Wound Stasis Dressing for Large Surface Wounds," which claims priority to U.S. Provisional Patent Application No. 61/525,036, filed Aug. 18, 2011 entitled "Wound Stasis Dressing for Large Surface Wounds," and to U.S. Provisional Patent Application No. 61/443,520, filed Feb. 16, 2011 entitled "Wound Stasis Dressing for Large Surface Wounds," the entire disclosures of which are hereby incorporated by reference in their entirety.

GOVERNMENT INTERESTS

This invention was made with United States government support under Contract No. W911NF-11-C-0038. The Government has certain rights in the invention.

TECHNICAL FIELD

Embodiments herein relate to methods, compositions and devices for controlling bleeding and treating wounds.

BACKGROUND

A leading cause of preventable battlefield death is bleeding. Although several wound dressing technologies are being marketed to control aggressive hemorrhages from severe external injuries, these devices are potentially ineffective against large soft tissue wounds in the calf, thigh, buttocks or shoulder that result in severe bleeding and the survival of the soldier is entirely dependent on immediate access to blood products and emergent surgical repair.

A principal method for treating bleeding wounds is to stop the flow of blood by applying pressure with a bandage to facilitate formation of a clot. However, current wound dressings are often too stiff and too rigid to fit into a narrow space of a cavity wound or, if sufficiently pliable, do not adequately conform to irregular tissues geometries to cause rapid and effective hemostasis. Bandage and gauze technologies are hard to pack and hold into these wounds and generally fail to adequately stop blood loss.

Granular and powder based hemostatic products have been employed to address the deficiency of current wound dressings for deep, irregular wounds, however, these products also have significant drawbacks. Hemostats in the form of powders, particulates or granules pose an unacceptable risk in forming emboli, are difficult to deploy in austere environments (e.g., environments that include wind, darkness, etc.), are susceptible to washing or migration away from the wound site, and are difficult to retrieve from the wound site at a place of definitive care. Additionally, granular and powder based hemostatic products are difficult to handle because they may have high electrostatic charge causing them to stick to instruments, gloves and tissues, thus preventing adequate penetration into irregular wound cavities. Also, in windy environments, powders or granules may be very difficult to get into the wound and may actually blow back into a caregiver's eyes. Powder or granule based hemostats also exhibit a lack of physical cohesion, making them unable to sufficiently withstand the chaotic fluid environments created by severe, high pressure bleeding. Thus, these granular and powder based hemostats may simply wash away before effectively contributing to hemostasis.

BRIEF DESCRIPTION OF THE DRAWINGS

Embodiments will be readily understood by the following detailed description in conjunction with the accompanying drawings and the appended claims. Embodiments are illustrated by way of example and not by way of limitation in the figures of the accompanying drawings.

FIG. 4 illustrates preparation of a hemostatic composition in accordance with various embodiments;

FIG. 5A illustrates a dressing with an integrated valve in accordance with various embodiments;

FIGS. 5B and 5C illustrate the use of a dressing to contain liquid-expandable articles introduced into a bleeding wound.

DETAILED DESCRIPTION OF DISCLOSED EMBODIMENTS

Figure 1A:
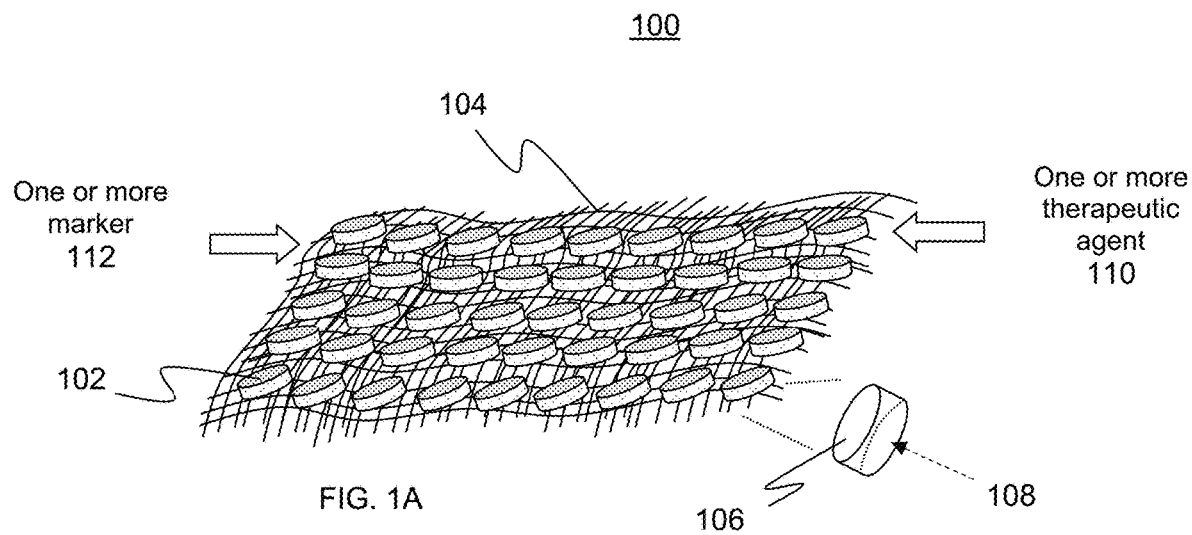
FIGS. 1A-1C illustrate hemostatic compositions and elements thereof in accordance with various embodiments.

In the following detailed description, reference is made to the accompanying drawings which form a part hereof, and in which are shown by way of illustration embodiments that may be practiced. It is to be understood that other embodiments may be utilized and structural or logical changes may be made without departing from the scope. Therefore, the following detailed description is not to be taken in a limiting sense, and the scope of embodiments is defined by the appended claims and their equivalents.

Various operations may be described as multiple discrete operations in turn, in a manner that may be helpful in understanding embodiments; however, the order of description should not be construed to imply that these operations are order dependent.

The description may use perspective-based descriptions such as up/down, back/front, and top/bottom. Such descriptions are merely used to facilitate the discussion and are not intended to restrict the application of disclosed embodiments.

The terms "coupled" and "connected," along with their derivatives, may be used. It should be understood that these terms are not intended as synonyms for each other. Rather, in particular embodiments, "connected" may be used to indicate that two or more elements are in direct physical or electrical contact with each other. "Coupled" may mean that two or more elements are in direct physical or electrical contact. However, "coupled" may also mean that two or more elements are not in direct contact with each other, but yet still cooperate or interact with each other.

For the purposes of the description, a phrase in the form "A/B" or in the form "A and/or B" means (A), (B), or (A and B). For the purposes of the description, a phrase in the form "at least one of A, B, and C" means (A), (B), (C), (A and B), (A and C), (B and C), or (A, B and C). For the purposes of the description, a phrase in the form "(A)B" means (B) or (AB) that is, A is an optional element.

The description may use the terms "embodiment" or "embodiments," which may each refer to one or more of the same or different embodiments. Furthermore, the terms "comprising," "including," "having," and the like, as used with respect to embodiments, are synonymous, and are generally intended as "open" terms (e.g., the term "including" should be interpreted as "including but not limited to," the term "having" should be interpreted as "having at least," the term "includes" should be interpreted as "includes but is not limited to," etc.).

With respect to the use of any plural and/or singular terms herein, those having skill in the art can translate from the plural to the singular and/or from the singular to the plural as is appropriate to the context and/or application. The various singular/plural permutations may be expressly set forth herein for sake of clarity.

Embodiments herein provide hemostatic compositions (also referred to as hemostatic dressings) comprising a plurality of liquid-expandable articles arranged on a backing material. In general, embodiments include methods for treating hemorrhagic injuries. More specifically, there is provided a method to effect rapid hemostatic response and control hemorrhage by introducing a hemostatic composition into a bleeding wound cavity. An embodiment also provides a method of preparing or manufacturing such a hemostatic composition.

In the following description, unless further particularized or otherwise noted, the term "liquid-expandable" is intended to refer to any material or substance that expands in occupied volume upon contact with a liquid.

Figure 1B:
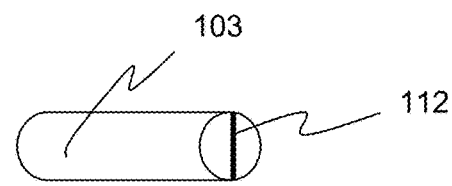
Figure 1C:
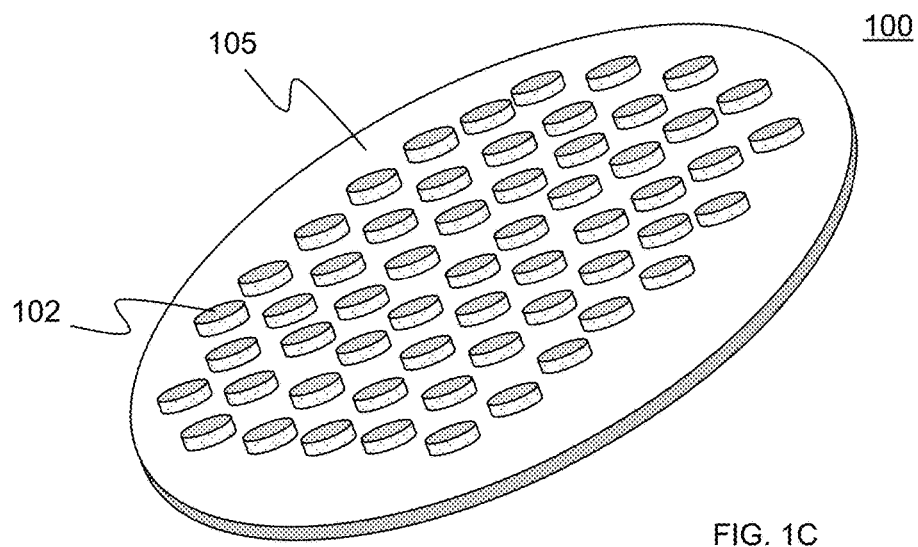

In an embodiment, a hemostatic composition comprises a plurality of liquid-expandable articles adapted to expand upon contact with a liquid, wherein the liquid expandable articles are disposed on a backing material. FIGS. 1A-1C illustrate selected aspects of hemostatic compositions. As shown, hemostatic composition 100 includes a plurality of liquid-expandable articles 102 disposed on backing material 104. As illustrated in FIG. 1A, backing material 104 appears flexible and porous.

Each liquid-expandable article 102 is adapted to expand into an expanded article upon contact with a liquid. It follows that a plurality of the liquid expandable articles 102 is adapted to expand into a plurality of expanded articles upon contact with a liquid. In various embodiments, the liquid may be an aqueous solution, such as a bodily fluid. For example, the liquid may be blood.

Once expanded, liquid-expandable articles 102 may be soft and pliable. Without being limited to any particular theory, this quality may permit the liquid-expandable articles 102 to conform to irregular wound crevices, gaps, and fissures.

In an embodiment, there is provided a hemostatic composition comprising a backing material having a surface, and a plurality of liquid-expandable articles disposed on the surface of the backing material, wherein the plurality of liquid-expandable articles are adapted to expand into expanded articles upon contact with a liquid and extend away from the surface of the backing material.

According to embodiments, hemostatic composition 100 comprises at least 3 liquid-expandable articles 102. In another embodiment, hemostatic composition 100 comprises at least 10 liquid-expandable articles 102. In yet another embodiment, hemostatic composition 100 comprises at least 50 liquid-expandable articles 102. In yet another embodiment, hemostatic composition 100 comprises at least 100 liquid-expandable articles 102.

In embodiments, the occupied volume of each liquid-expandable article 102 may be from $0.7 \text{ mm}^3$ to $7000 \text{ mm}^3$, such as from $500 \text{ mm}^3$ to $5000 \text{ mm}^3$. In various embodiments, the volume of each liquid-expandable article 102 may be greater than $1 \text{ mm}^3$. In various embodiments, the volume of each liquid-expandable article 102 may be greater than $5 \text{ mm}^3$. In various embodiments, the volume of each liquid-expandable article 102 may be greater than $10 \text{ mm}^3$. In various embodiments, the volume of each liquid-expandable article 102 may be greater than $50 \text{ mm}^3$. In various embodiments, the volume of each liquid-expandable article 102 may be greater than $100 \text{ mm}^3$.

In various embodiments, liquid-expandable articles 102 on backing material 104 may all be uniform in size of may comprise a mixture of sizes. In an embodiment, liquid-expandable articles 102 may each have the same diameter, but may have different lengths. Alternatively, the diameters may vary among the liquid-expandable articles 102. Combinations of the above are also provided.

According to various embodiments, an expanded article 103 occupies a volume greater than a liquid-expandable article 102. In various embodiments, the average volume ratio of liquid-expandable articles to expanded articles is at least 4×. In other embodiments, the average volume ratio of liquid-expandable articles to expanded articles is at least 8×. In other embodiments, the average volume ratio of liquid-expandable articles to expanded articles is at least 10×. In other embodiments, the average volume ratio of liquid-expandable articles to expanded articles is at least 12×.

In various embodiments, liquid-expandable articles 102 may be capable of expanding to 80% or greater of their maximum expansion capacity in 60 seconds or less following immersion in liquid. In other embodiments, liquid-expandable articles 102 may be capable of expanding to 80% or greater of their maximum expansion capacity in 30 seconds or less following immersion in liquid. In other embodiments, liquid-expandable articles 102 may be capable of expanding to 80% or greater of their maximum expansion capacity in 10 seconds or less following immersion in liquid. In other embodiments, liquid-expandable articles 102 may be capable of expanding to 80% or greater of their maximum expansion capacity in 5 seconds or less following immersion in liquid.

Liquid-expandable articles 102 may comprise one or more predetermined shapes, based on adjustments to the length, width, diameter, or cross-sectional shape. Without being limited by theory, the shape, size and/or pattern of liquid-expandable articles 102 may influence the pliability of flexible backing 104, as well as the ability of the hemostatic composition to fit into, expand, fill, partially fill and conform to a wound cavity. In addition, the shape may assist expanded articles in retaining a desired position in the wound cavity. In FIGS. 1A-1C, liquid-expandable articles 102 are depicted as a cylindrical shape. This notwithstanding, the predetermined shape of liquid-expandable articles 102 may include other articles with round, triangular, rectangular, hexagonal, conical, or octagonal cross-sections. In various embodiments, predetermined shapes having multiple projections (e.g., a star) may be used. In other embodiments, hemostatic composition 100 may comprise liquid-expandable articles 102 with haphazard, random, irregular, or jagged shapes. In various embodiments, hemostatic composition 100 may comprise liquid-expandable articles 102 of two or more predetermined shapes. In other embodiments, hemostatic composition 100 may have liquid-expandable articles 102 comprising a mixture of predetermined shapes and/or irregular shapes.

As shown in FIG. 1A, the predetermined shape of liquid-expandable articles 102 may define any shape having first major outer surface 106 and a second major outer surface 108. In various embodiments, the average distance between the outer surfaces may be from 0.5 mm to 20 mm. In various embodiments, the average distance between a first major outer surface 106 and a second major outer surface 108 may be from 1 mm to 10 mm. For such embodiments, the average distance between the first major outer surface 106 and the second major outer surface 108 may be from 1 mm to 5 mm.

According to various embodiments, liquid-expandable articles 102 may be substantially in the form of a disk or cylinder. For such embodiments, the average diameter of the first major outer surface 106 and the second major outer surface 108 may be from 1 mm to 20 mm. The average diameter of the first major outer surface 106 and the second major outer surface 108 may be from 5 mm to 10 mm. In various embodiments, hemostatic composition 100 may comprise liquid-expandable articles 102 having the same average diameter or a mixture of liquid-expandable articles 102 having different average diameters.

In various embodiments, the liquid-expandable articles 102 may comprise an absorbent material including, but not limited to, a sponge or fibrous material. In various embodiments, the absorbent material may comprise a polysaccharide such as, but not limited to, cellulose, starch, chitin, or chitosan. In various embodiments, liquid-expandable articles 102 may be biodegradable and/or bioabsorbable. In some embodiments, the liquid-expandable articles 102 may not comprise oxidized cellulose. In various embodiments, the absorbent material may comprise synthetic sponges such as, but not limited to, various polyvinyl alcohol (PVA) polymers and derivatives thereof having desirable physical and mechanical properties.

In various embodiments, liquid-expandable articles 102 may comprise a compressed material. For these embodiments, and without being limited to any particular theory, the compressed material, when hydrated, may rapidly expand in an effort to assume its pre-compression dimensions. In this way, liquid-expandable articles 102 may store additional mechanical energy in a compressed state, as compared to the non-compressed state, that is released when exposed to a liquid, thus causing liquid-expanding articles 102 to quickly expand. The absorbent material can be compressed by heat compression or any other suitable compression method known in the art.

In various embodiments, hemostatic composition 100 may further comprise one or more therapeutic agents 110. In an embodiment, the liquid-expandable articles 102 may be impregnated with the one or more therapeutic agents 116. In another embodiment, the liquid-expandable articles 102 may be suffused with one or more therapeutic agents 110. In another embodiment, the liquid-expandable articles 102 may be coated with one or more therapeutic agents 110. In yet another embodiment, the one or more therapeutic agents 110 may be dispersed throughout liquid-expandable articles 102. In embodiments, the one or more therapeutic agents 110 may be provided only on liquid-expandable articles 102, only on backing material 104, or a combination of both.

The one or more therapeutic agents 110 may be selected from the group consisting of analgesics, steroids, antihistamines, anesthetics, bactericides, disinfectants, fungicides, vasoconstrictors, chemotherapeutic drugs, antibiotics, keratolytics, cauterizing agents, antiviral drugs, epidermal growth factor, fibroblast growth factors, transforming growth factors, glycoproteins, fibrinogen, fibrin, humectants, preservatives, lymphokines, cytokines, odor controlling materials, vitamins, and clotting factors.

In various embodiments, the one or more therapeutic agents 110 may include hemostatic agent(s). For example, the one or more therapeutic agents 110 may include chitosan or a derivative of chitosan. In other embodiments, the one or more therapeutic agents 110 may include kaolin. In other embodiments, the one or more therapeutic agents 110 may be selected from the group consisting of diatomaceous earth, silica, clays, minerals, attapulgite, bentonite, zeolite, and bioactive glasses.

According to various embodiments, the one or more therapeutic agents 110 may include an inorganic salt. Examples of an inorganic salt include, but are not limited to, a divalent ion selected from the group consisting of zinc, copper, magnesium, calcium and nickel, as well as CaO, $CaCl_2$, $AgNO_3$, $Ca(NO_3)_2$, $Mg(NO_3)_2$, $Zn(NO_3)_2$, $NH_4NO_3$, AgCl, $Ag_2O$, zinc acetate, magnesium acetate, calcium citrate, zinc citrate, magnesium citrate, magnesium chloride, magnesium bromide, zinc chloride, zinc bromide, calcium bromide, calcium acetate and calcium phosphate.

In various embodiments, hemostatic composition 100 may comprise one or more marker 112 for identifying the location of the dressing in a wound and facilitating removal of the dressing from the wound. For such embodiments, marker 112 may be coupled to backing 104. In other embodiments, a liquid-expandable article 102 or expanded article 103 may comprise a marker 112. Marker 112 may comprise a radio-frequency identification (RFID) tag. In other embodiments, marker 112 may comprise a radiopaque material. For example, marker 112 may comprise a radiopaque filament, bead, ball, sphere, wire, or strip. For example, marker 112 may comprise a barium sulfate-infused polymer, such as polypropylene. In other embodiments, at least a portion of hemostatic composition 100 may be suffused with a radiopaque material. In yet another embodiment, at least a portion of hemostatic composition 100 may be coated with a radiopaque material.

A backing material may be a porous or non-porous material. FIG. 1A illustrates a porous backing material 104. FIG. 1C illustrates a non-porous backing material 105, such as polyurethane, polyethylene, and/or silicone films or sheets. Exemplary porous materials may include fabrics, meshes and/or gauzes. For example, the porous backing material can be made of fabrics, nonwoven fabrics, melt-blown webs, foams, spun-bonded webs, thermal-bonded webs, spun-laced webs, paper, and/or thermally-embossed nonwoven fabrics. More precisely, examples of the substrate may be woven fabrics; knitted fabrics; or non-woven fabrics of an organic polymer such as cotton, polyvinyl alcohol, or cellulose; paper; and perforated films of polyvinyl alcohol. The substrate may be elastic or non-elastic.

In an embodiment, a backing material may be an occlusive dressing.

According to embodiments, liquid-expandable articles 102 may be arranged on a backing material in a predetermined pattern. Such a pattern may mimic a wound site or provide alternative size and configurations of groupings of liquid-expandable articles 102 to apply to a given wound. In embodiments, the liquid-expandable articles form a 3-dimensional array on top of a backing material. The attachment points of the liquid-expandable articles may, in an embodiment, by substantially coplanar with each other.

According to embodiments, liquid-expandable articles 102 may be disposed on one side of the backing material. In other embodiments, liquid-expandable articles 102 may be disposed on both sides of the backing material.

According to embodiments, liquid-expandable articles 102 may be disposed to the backing material with an adhesive. Exemplary adhesives include cyanoacrylates, epoxies, light cure adhesives, silicones, urethanes hydro gels, acrylics, silicone gels, silicone PSA and hydrocolloids. Other mechanisms may be used to secure liquid-expandable articles 102 to the backing material such as molding, stitching, etc.

In an embodiment, the adhesive is designed to dissolve, delaminate, or otherwise lose its adhesive property as a result of sufficient contact with fluid. Exemplary adhesives with this quality may include hydrogel, acrylic, silicone gel, silicone PSA, hydrocolloid, etc. As a result, when liquid-expandable articles are coupled to a backing material using such an adhesive and then contacted with a fluid, the liquid-expandable articles may detach from the backing material. In such embodiments, the liquid-expandable articles and expanded articles become mechanically uncoupled from one another and the backing material and therefore may be capable of moving independently from one another. Without being limited by theory, this quality may permit the liquid-expandable articles and expanded articles to pass through narrow wound openings and to spread into irregular wound crevices, gaps and fissures within the wound. In addition, by detaching during use, the backing material may be separately removed from the wound to permit inspection of the wound or changing of the outer dressing (backing material) without dislodging the expanded articles from the wound.

In an embodiment, the backer material and the liquid-expandable articles are constructed from different materials. In an embodiment, the backer material and the liquid-expandable articles are constructed from the same material.

In an embodiment, a unitary construct having a backing component and a plurality of liquid-expandable articles (protrusions) may be provided. In such an embodiment, the two components of the construct are made of the same material, but are designed for different purposes. The backing component provides support for the liquid-expandable protrusions. As the backing component is made from the same material as the liquid-expandable protrusions, the backing component would also undergo expansion in response to liquid contact. In an embodiment, the backing component could be compressed to a lesser degree than the protrusions, such as providing a compression ratio of from 2:1 to 5:1 (protrusions:backing). In embodiments, the backing may be formed relatively thin so as to provide support but retain flexibility. A suitable thickness of the backing (prior to liquid contact) would be approximately 1-5 mm.

The liquid-expandable protrusions are design to extend into various smaller areas of a wound. The liquid-expandable protrusions may be formed in any suitable number, and may have a variety of shapes and sizes as discussed elsewhere in this disclosure.

In an embodiment, the construct may be formed by molding or etching, such as laser etching, a shaped element.

According to embodiments, hemostatic composition 100 may comprise adhesive for securing a portion of the backing material to a patient's skin. Suitable adhesives for adhering the backing material to the patient's skin include hydrogel, acrylic, silicone gel, silicone PSA, hydrocolloid, etc.

In an embodiment, there is provided a method to effect rapid hemostatic response and hemorrhage control by applying a hemostatic composition to a bleeding wound.

Figure 2:
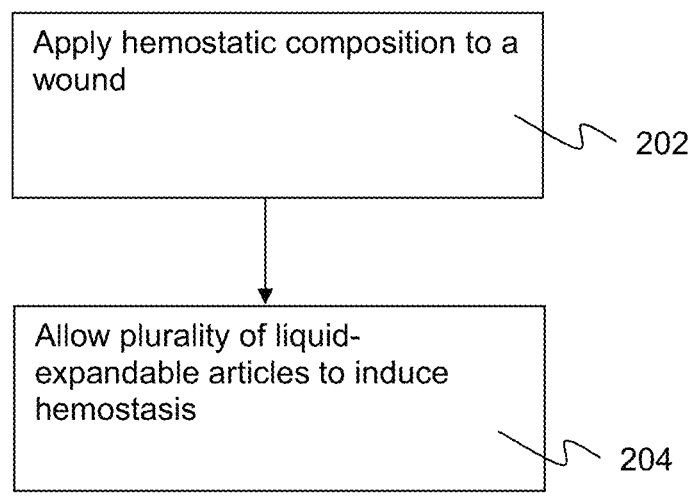
FIG. 2 illustrates a block diagram of treating a wound with a dressing in accordance with various embodiments.

FIG. 2 is a block diagram depicting a method for treating hemorrhagic injuries in accordance with embodiments herein. As illustrated, at 202, hemostatic composition 100 is applied to a wound. At 204, the plurality of liquid-expandable sponges 102 expand and are allowed to induce hemostasis. For example, hemostatic composition 100 may be delivered into a wound cavity, the liquid-expandable articles 102 allowed to contact blood within the cavity and subsequently expand into expanded articles, which generally conform to a shape defined by at least a portion of the wound cavity.

Applying a hemostatic composition to a wound may comprise applying the hemostatic composition by hand. The hemostatic composition may be applied onto a wound using a securing adhesive. In another embodiment, the hemostatic composition may be wrapped around a wound site, such as around an arm, leg, torso, etc.

Exemplary wounds often arise from, but are not limited to, traumatic accidents, projectiles from weapons or improvised explosive devices which may create large soft tissue wounds in the calf, thigh, buttocks or shoulder that result in severe bleeding. Such wounds may be associated with an arterial puncture, a venous puncture, an arterial laceration and/or a venous laceration.

Each wound can have a unique size and/or shape. Often, the extent of the tissue damage cannot be determined until emergent care can be provided. The use of hemostatic composition 100 allows for the treatment of several wound types.

Figure 3A:
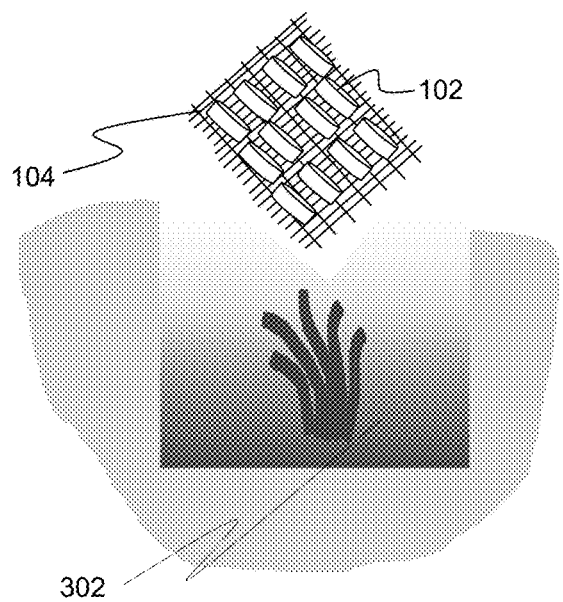
FIGS. 3A-3D illustrate methods for treating a bleeding wound employing hemostatic compositions in accordance with various embodiments.

FIG. 3A illustrates a method for treating hemorrhagic injuries in a living being employing the medical device of FIG. 1A. As illustrated in FIG. 3A, hemostatic composition 100 may be applied to wound 302. Once in the wound, liquid-expandable articles 102 contact blood and expand into expanded articles.

Figure 3B:
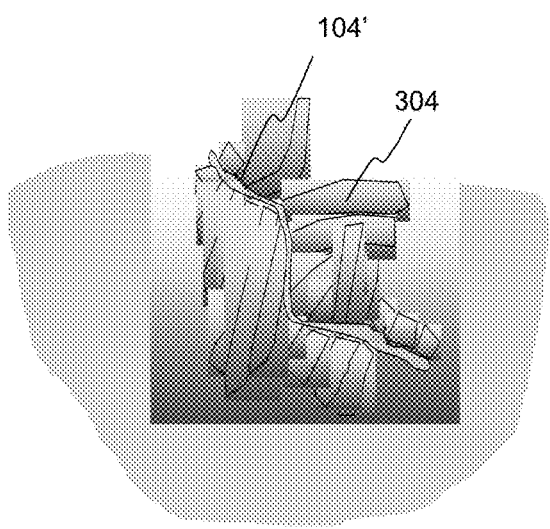

Expanded articles 304 are illustrated in FIG. 3B, in which expanded articles 304 fill the cavity and induce hemostasis. FIG. 3B also illustrates a hemostatic composition (slightly modified from composition 100), in which backing material 104' has expanded articles 304 on both sides of backing material 104'.

Figure 3C:
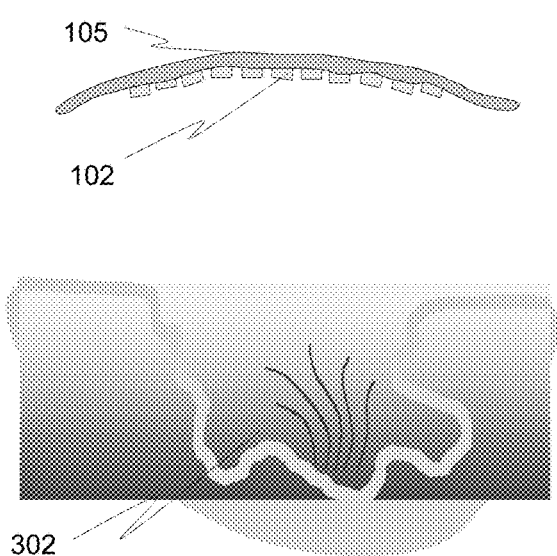
Figure 3D:
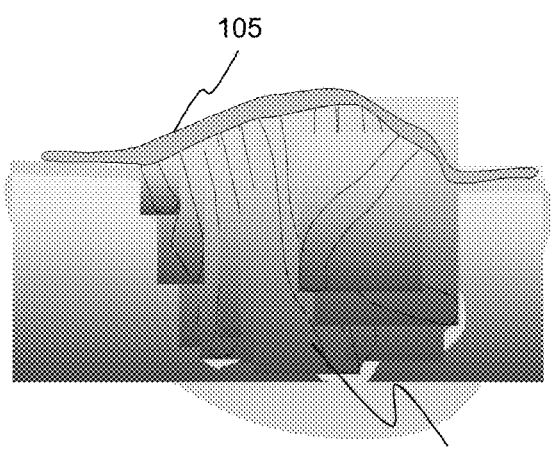

FIGS. 3C and 3D illustrate a method for treating hemorrhagic injuries in a living being employing the medical device of FIG. 1C. As illustrated in FIG. 3C, hemostatic composition 100 may be applied to wound 302. Once in the wound, liquid-expandable articles 102 contact blood and expand into expanded articles 304. As shown in FIG. 3D expanded articles fill the cavity and induce hemostasis.

A method of preparing a hemostatic composition in accordance with embodiments is also provided. FIG. 4 generically depicts a method of manufacturing a hemostatic composition. At 402, liquid-expandable articles may be prepared by forming an absorbent material into liquid-expandable articles. At 404, the liquid-expandable articles are arranged into a predetermined pattern and disposed on a backing material. In other embodiments, the liquid-expandable articles may be co-formed, such as co-molded, with the backing material.

For various embodiments, forming the absorbent material into a plurality of liquid-expandable articles may include compressing the absorbent material into a liquid-expandable material. This may be accomplished, for example, using conventional mechanical compression techniques well known to those skilled in the art. In other embodiments, compressing the absorbent material into a liquid-expandable material may comprise freeze-drying the absorbent material.

Forming the absorbent material into a plurality of liquid-expandable articles may include forming it into desirable shapes and sizes. For such embodiments, the liquid-expandable material may be cut using, for example, a die and press. The absorbent material may also be molded directly into desired shapes and sizes.

In various embodiments, the absorbent material may be formed into a plurality of liquid-expandable articles by extrusion, pelletization, briquetting, tabletting, or other methods familiar to those skilled in the art. Alternatively, the absorbent material may be mechanically crushed into irregular shaped lumps, with desirable size ranges to be separated out by a classifier.

The absorbent material may be combined with one or more therapeutic agents prior to, during or subsequent to being formed into liquid-expandable articles. The combining of absorbent material with one or more therapeutic agent may be performed by impregnating, suffusing, coating or dispersing the one or more therapeutic agents on or throughout the absorbent material. In an embodiment, the therapeutic agent may be sprayed onto the absorbent material. In another embodiment, the absorbent material may be soaked in a therapeutic agent solution. The one or more therapeutic agents may be selected from the group disclosed above.

In further embodiments, a marker may be applied to each of the liquid-expandable articles. This may be accomplished in a number of ways. For example, the marker may be imbedded in the absorbent material prior to forming the absorbent material into liquid-expandable articles. Alternatively, the marker may be imbedded in the liquid-expandable articles during or following a formation step. In another embodiment, a radiopaque material may be coated or suffused onto the absorbent material before, during or after formation of the liquid-expandable articles. For such embodiments, the marker may be selected from the markers disclosed above.

Once liquid-expandable articles have been prepared, they may be disposed on a backing material. Disposing liquid-expandable articles on a backing material may comprise using an adhesive. Exemplary adhesives include cyanoacrylates, epoxies, light cure adhesives, silicones, urethanes hydrogels, acrylics, silicone gels, silicone PSA, and hydrocolloids.

In an alternative embodiment, a suitable dressing may be configured with a valve through which liquid-expandable articles may be introduced. The modified dressing is applied over the wound to keep the liquid-expandable articles contained within the wound site.

FIG. 5A illustrates a dressing 502 with an integrated valve 504. FIGS. 5B and 5C illustrate the use of dressing 502 to contain liquid-expandable articles 102 introduced into a bleeding wound 506. An applicator 508 is employed to facilitate the storage, handling and/or application of liquid-expandable articles 102. As illustrated, liquid-expandable articles 102 may be introduced to wound 506 using applicator 508. For such embodiments, liquid-expandable articles 102 may be ejected or otherwise dispensed from applicator 508. In an exemplary embodiment, wound 506 defines a cavity with an opening and a cavity boundary and includes at least one bleeding vessel. Once in the wound, liquid-expandable articles 102 contact blood and expand into expanded articles 510. As shown in FIG. 5C, expanded articles 510 fill the cavity and induce hemostasis. Dressing 502 serves to restrict migration of liquid-expandable articles 102 out of wound 506 during and after expansion.

In embodiments, valve 504 may be a one-way or a two-way valve. As a one-way valve, there is an additional mechanical force provided to restrict migration of the articles from the wound. The valve may be constructed from any suitable material such as a plastic, rubber, or fabric. In embodiments, the valve may be coupled to dressing 502 using adhesive or another bonding mechanism such as molding or stitching.

Thus, in an embodiment, there is provided a hemostatic dressing comprising a backing material having a first side and a second side, and a valve disposed within the backing material providing passage from the first side of the backing material to the second side of the backing material for introduction of one or more elements through the valve.

In such embodiments, the hemostatic composition comprises a plurality of liquid-expandable articles that are mechanically uncoupled from one another and therefore may be capable of moving independently from one another. Without being limited by theory, this quality may permit the liquid-expandable articles to pass through narrow wound openings and to spread into irregular wound crevices, gaps and fissures. Alternatively, the liquid-expandable articles may be coupled together by a string or a weak bonding adhesive or other element to permit independent movement of the liquid-expandable articles when introduced into a wound.

Figure 6:
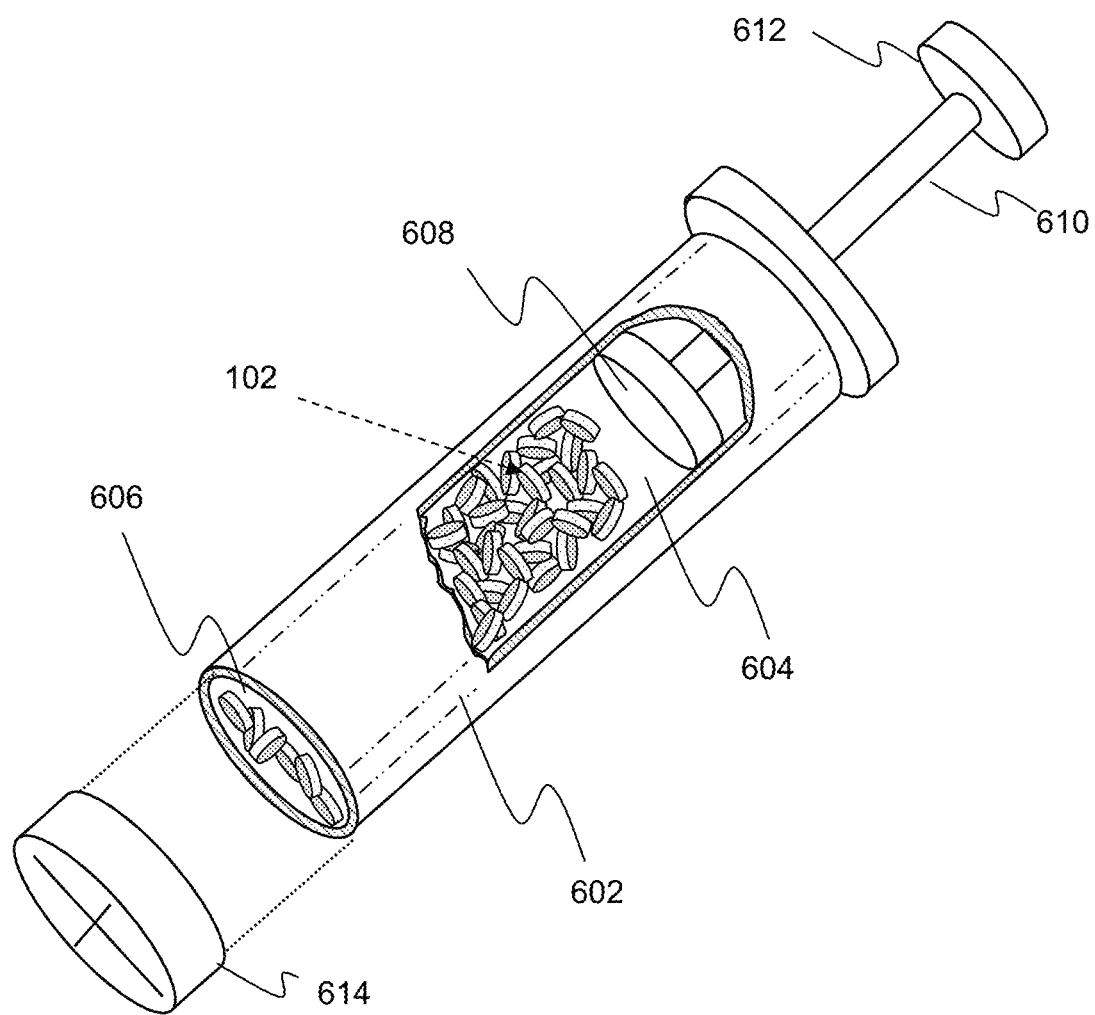
FIG. 6 illustrates an applicator for use in accordance with various embodiments.

FIG. 6 further illustrates an applicator for use in accordance with embodiments herein. As shown, applicator 602 includes a receptacle 604 with an output end 606 and a moveable piston 608 positioned in receptacle 604. Liquid-expandable articles 102 are positioned in receptacle 604. According to various embodiments, receptacle 604 may be a tube.

In one form, receptacle 604 may comprise a plastic. For example, receptacle 604 may comprise PEEK, PEKK, Polyetherimide (PEI), Polyethersulfone (PES), Polyetherimide (PEI), Polyimide (TPI), FEP, FEP 100, ETFE, ETFE 207, ECTFE, PFA or PTFE. In other embodiments, receptacle 604 may comprise a filled plastic or a polymer composite.

Moveable piston 608 is employed to facilitate the ejection of the plurality of liquid-expandable articles 102 from receptacle 604 through output end 606. In an embodiment, moveable piston 608 may be coupled to shaft 610, which has a handle 612. In other embodiments, moveable piston 608 may be coupled to a spring or other similar force-applying element.

In accordance with various embodiments, applicator 602 may include a valve 614 coupled to receptacle 604 at output end 606. Valve 614 is employed to prevent the premature exit of liquid-expandable articles 102 from receptacle 604, as well as impede the flow of liquid into receptacle 604 prior to the ejection of liquid-expandable articles.

In various embodiments, applicator 602 may be included in a kit, preloaded with liquid-expandable articles 102, with dressing 502 having an integrated valve 504. A typical kit may comprise instructions, such as a product insert or label, directing the user to prepare and administer liquid-expandable articles 102 and dressing 502 to a wound.

Embodiments herein also provide for treatment of a living being having a body with a wound defining a cavity with a volume bounded by a surface through which blood is flowing into the cavity, the cavity having an entry opening that is in communication with the cavity; and a plurality of expandable articles that each have a starting volume and a second volume that is greater than the starting volume, the plurality of expandable articles with the starting volume deliverable through the entry opening into the cavity and upon being exposed to fluid in the cavity expanding to the second volume, the plurality of expandable articles within the cavity and expanding to the second volume collectively inducing hemostasis.

Embodiments provide a composition comprising a plurality of small, liquid-expandable articles that are configured to induce hemostasis when contacted with blood and can be applied in deep, irregular wounds. The plurality of liquid-expandable articles possess an ability, upon contact with blood, to rapidly expand to form a pliable, shapeable, conformable and crevice-filling mass. In an embodiment, the plurality of liquid-expandable articles expand at substantially the same rate and to substantially the same extent.

Without limiting the scope of the disclosure, this mass may exert mechanical pressure on the surface of the wound, as well as interact with blood components to ultimately facilitate the formation of a fluid arresting coagulum within the wound cavity. The combination of mechanical pressure and enhanced clotting makes the composition able to curtail bleeding without the application of external compression. In other embodiments, liquid-expandable articles may be capable of expanding through a swelling mechanism.

While it is noted above that external compression is not necessary, in embodiments, external compression may be used in conjunction with the hemostatic composition. Such external compression may be provided by an elastic backing material or by a separate elastic or compression material/device.

Without limiting the scope of the disclosure, compositions herein may be advantageous for several reasons. The liquid-expandable articles have the ability to quickly expand into expanded articles. This allows the expanded articles to quickly fill the wound cavity and provide a rapid hemostatic effect. Additional advantages associated include improved positioning within the wound, improved tissue apposition, and better conformation to intricate wound contours. The soft, pliable nature of the expanded articles, in connection with spring-like characteristics, permits the expanded articles to provide a gentle outward pressure within the wound cavity, without the need to apply excessive pressure that can compromise perfusion to local tissues. Because the expanded articles conform to the wound cavity, pressure is exerted multi-directionally to address all bleeding points. The ability to exert outward pressure against and closely conforming to surrounding tissue surfaces helps the expanded articles maintain positioning within the wound cavity in the face of high flow arterial bleeding and deformation during transport of the injured person, maximize the contact and application of material at the sources of bleeding, and ensure constant and gentle, yet effective, compression within the wound cavity (without creating harmful pressure points).

Although certain embodiments have been illustrated and described herein, it will be appreciated by those of ordinary skill in the art that a wide variety of alternate and/or equivalent embodiments or implementations calculated to achieve the same purposes may be substituted for the embodiments shown and described without departing from the scope. Those with skill in the art will readily appreciate that embodiments may be implemented in a very wide variety of ways. This application is intended to cover any adaptations or variations of the embodiments discussed herein. Therefore, it is manifestly intended that embodiments be limited only by the claims and the equivalents thereof.

The invention claimed is:

1. A method of treating a bleeding wound having a bleeding wound cavity, comprising:
    introducing a hemostatic composition into the bleeding wound cavity, the hemostatic composition comprising,
        a continuous sheet of backing material having a surface, the continuous sheet of backing material being sufficiently pliable to conform to the wound; and
        a plurality of liquid-expandable articles, wherein the liquid-expandable articles comprise compressed sponges, each individual liquid-expandable article having a first end attached to the surface of the continuous sheet of backing material at a corresponding attachment point and a second, opposing end extending away from the surface of the continuous sheet of backing material,
    wherein:
        the plurality of liquid-expandable articles are arranged in a three-dimensional array on the surface of the continuous sheet of backing material, such that a first plurality of liquid-expandable articles are disposed laterally along the surface of the continuous sheet of backing material and a second plurality of liquid-expandable articles are disposed longitudinally along the surface of the continuous sheet of backing material, and
        permitting contact between the hemostatic composition and blood within the bleeding wound cavity such that the plurality of liquid-expandable articles expand into expanded articles and the second end extends farther away from the surface of the continuous sheet of backing material,
        wherein the plurality of liquid-expandable articles store mechanical energy in a compressed state and the plurality of liquid-expandable articles release stored mechanical energy and mechanically expand into elongate expanded articles upon contact with blood, wherein a volume of the expanded articles is at least 4 times a volume of the liquid-expandable articles, and wherein the liquid-expandable articles expand to 80% or greater of their maximum expansion capacity in 30 seconds or less following immersion in blood.

2. The method of claim 1, wherein the hemostatic composition further comprises one or more therapeutic agents coupled to at least one of the continuous sheet of backing material and the plurality of liquid-expandable articles.

3. The method of claim 1, wherein the liquid-expandable articles comprise cellulose.

4. The method of claim 1, wherein the hemostatic composition further comprises one or more hemostatic agents coupled to at least one of the continuous sheet of backing material and the plurality of liquid-expandable articles.

5. The method of claim 1, wherein each liquid-expandable article within the plurality of liquid-expandable articles comprises a marker.

6. The method of claim 1, wherein the continuous sheet of backing material comprises a marker.

7. The method of claim 1, wherein the expanded articles at least partially fill the bleeding wound cavity.

8. The method of claim 1, wherein the surface of the continuous sheet of backing material is a first surface, the continuous sheet of backing material further comprises a second surface, and wherein a second plurality of liquid-expandable articles are each individually coupled to the second surface of the continuous sheet of backing material.

9. The method of claim 1, wherein individual expanded articles have a lateral dimension and a longitudinal dimension, wherein the longitudinal dimension is greater than the lateral dimension, and wherein the longitudinal dimension extends away from the surface of the continuous sheet of backing material.

10. The method of claim 1, wherein the first ends of the plurality of liquid-expandable articles are attached to the surface of the continuous sheet of backing material with an adhesive.

11. The method of claim 1, wherein the plurality of liquid-expandable articles are attached to the surface of the continuous sheet of backing material in a predetermined arrangement.

12. The method of claim 1, wherein the first ends of the plurality of liquid-expandable articles are attached to the surface of the continuous sheet of backing material at respective attachment points, and wherein the attachment points are substantially co-planar.

13. The method of claim 1, wherein the continuous sheet of backing material is porous.

14. The method of claim 13, wherein the continuous sheet of porous backing material is fabric, mesh, or gauze.

* * * * *